United States Patent
Tripathi et al.

(10) Patent No.: US 12,403,102 B2
(45) Date of Patent: Sep. 2, 2025

(54) PHARMACEUTICAL COMPOSITIONS CONTAINING PARACETAMOL DERIVATIVES AND USE THEREOF

(71) Applicant: M/S Status Projects Private Limited, Indore (IN)

(72) Inventors: Vinayshankar Tripathi, Indore (IN); Akshay Nikhil Patel, Indore (IN)

(73) Assignee: M/S Status Projects Private Limited, Indore (IN)

( * ) Notice: Subject to any disclaimer, the term of this patent is extended or adjusted under 35 U.S.C. 154(b) by 0 days.

(21) Appl. No.: 17/954,557

(22) Filed: Sep. 28, 2022

(65) Prior Publication Data

US 2024/0115522 A1   Apr. 11, 2024

(51) Int. Cl.
*A61K 31/136* (2006.01)
*A61K 9/00* (2006.01)

(52) U.S. Cl.
CPC .......... *A61K 31/136* (2013.01); *A61K 9/0056* (2013.01)

(58) Field of Classification Search
CPC ..... A61K 31/136; A61K 9/0056; A61K 31/00
See application file for complete search history.

(56) References Cited

U.S. PATENT DOCUMENTS 4,999,457 A * 3/1991 Fruchey ............... C07C 233/25
564/223

OTHER PUBLICATIONS

Rao RN, Narasaraju A. Rapid separation and determination of process-related substances of paracetamol using reversed-phase HPLC with photo diode array as a detector. Anal Sci. Feb. 2006;22(2):287-92. doi: 10.2116/analsci.22.287. PMID: 16512424. (Year: 2006).*
James LP, Mayeux PR, Hinson JA. Acetaminophen-induced hepatotoxicity. Drug Metab Dispos. Dec. 2003;31(12):1499-506. doi: 10.1124/dmd.31.12.1499. PMID: 14625346. (Year: 2003).*
IARC Working Group on the Evaluation of Carcinogenic Risks to Humans. Pharmaceuticals. Lyon (FR): International Agency for Research on Cancer; 2012. (IARC Monographs on the Evaluation of Carcinogenic Risks to Humans, No. 100A.) Phenacetin. Available from: https://www.ncbi.nlm.nih.gov/books/NBK304337/ (Year: 2012).*

* cited by examiner

*Primary Examiner* — Danah Al-Awadi
*Assistant Examiner* — Chantal Adlam
(74) *Attorney, Agent, or Firm* — Raj S. Dave; Dave Law Group LLC

(57) ABSTRACT

Disclosed are pharmaceutical compositions containing derivatives of paracetamol, such as 3-chloro-4-hydroxy-acetanilide, that exhibit enhanced potency and/or reduced hepatotoxicity in mammals, particularly humans. Also disclosed are investigational new drugs containing superior pharmacological versions of paracetamol which provide analgesic, antipyretic and antiphlogistic properties.

20 Claims, No Drawings

PHARMACEUTICAL COMPOSITIONS CONTAINING PARACETAMOL DERIVATIVES AND USE THEREOF

FIELD OF THE INVENTION

The present invention relates to derivatives of paracetamol (acetaminophen) and uses thereof. More particularly, the present invention is directed to pharmaceutical compositions containing derivatives of paracetamol, such as 3-chloro-4-hydroxy-acetanilide, that exhibit enhanced potency and/or reduced hepatotoxicity in mammals, particularly humans.

BACKGROUND

Paracetamol (also known as acetaminophen, N-acetyl-p-aminophenol and N-para-hydroxy-phenylacetamide) is an active ingredient that has been used for many years to relieve mild to moderate pain and/or fever. Paracetamol has the following chemical structure:

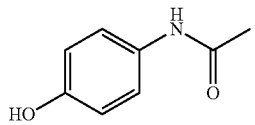

Although its mechanism of action is still not known in detail, paracetamol is one of the most widely used medicinal products in the world due to its very favorable risk-benefit ratio. Paracetamol is commonly administered in doses of 500 mg.

The favorable risk-benefit ratio of paracetamol, however, has made its use too common, leading to many accidental overdoses. This is particularly true in the US, where this compound is systematically added to over-the-counter (OTC) and prescription drug formulations. Consumers taking several medicinal products can thus eventually induce overdoses and fatal poisonings.

Paracetamol is found to have another major drawback in that, in order to be effective, it consumes a number of liver enzymes to metabolise. Paracetamol is a systematic evolution of analgesic drugs like acetanilide, indapamide, and indomethacin. It is natural to expect that the structure-activity relationship (SAR) of paracetamol has not been clearly understood so far. Therefore, the interplay of calcium channels, sodium channels, and potassium channels should be clearly understood in light of modern scientific advances and to correlate them with the pharmacological activities of paracetamol.

Once the structure-activity of paracetamol has been understood, it will make the inroads into further development of superior pharmacologically active investigational new drugs, much more amenable and probable. In today's medical science, the drugs which can relieve pain are manifold and many. Opioids, non-opioids, benzodiazepines, non-benzodiazepines, acetamides, non-acetamide, NSAIDs and non-NSAIDs etc. There is a never-ending chemical jargon in which the overall understanding of the pain management in the human body has perhaps been either lost or needs reinvention. It is desired to observe a couple of drugs and their modus operandi in the human body.

Paracetamol is known to step up the pain threshold by working on the prostaglandins. Ibuprofen does it by acting on the medulla oblongata, which is the joint of brain and the spinal cord. Likewise, benzodiazepines, opioids and non-opioids do the same by depressing the central nervous system (CNS). Almost all the names mentioned above are either habit-forming or cause drug dependence. It is only paracetamol which is generally accepted and known to not cause any drug dependence or habit forming. But involving P450 enzymes of the liver makes paracetamol unsuitable when a person is in primary, secondary or tertiary healthcare. In other words, paracetamol is not the drug of choice when a person needs it the most.

The United States Food and Drug Administration (FDA) has in fact alerted pharmaceutical companies to reduce doses of paracetamol in combination products. Moreover, in 2014, the FDA banned the marketing of all products combined with other active ingredients containing more than 325 mg of paracetamol, in order to limit the risk of poisoning and fatal accidents. According to current medical catalogues, an ideal antipyretic, analgesic and antiphlogistic is not available.

So, there is a strong need for a new drug which takes into its cognizance almost everything which is known so far and yet to pave the way for results which have not been achieved thus far by the medical fraternity.

For at least the above reasons, there is a need for medicinal products which exhibit the same therapeutic benefits of paracetamol, but at lower doses in order to reduce potential toxicity while maintaining efficacy.

SUMMARY OF THE INVENTION

It is therefore an object of the present invention to provide compositions that exhibit the same therapeutic profile as paracetamol, but at much lower doses and/or with substantially less side effects such as hepatotoxicity.

In accordance with these and other objects, a first embodiment of the present invention is directed to a pharmaceutical composition containing, as the active ingredient, an effective amount of a compound of the formula:

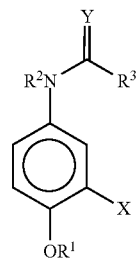

wherein
$R^1$ is hydrogen, $C_1$-$C_6$ alkyl, $C_2$-$C_6$ alkenyl, $C_2$-$C_6$ alkynyl, $C_2$-$C_7$ acyl, or $C_1$-$C_6$ aralkyl;
$R^2$ is hydrogen, $C_1$-$C_6$ alkyl, $C_2$-$C_6$ alkenyl, or $C_2$-$C_6$ alkynyl;
$R^3$ is $C_1$-$C_6$ alkyl, $C_2$-$C_6$ alkenyl, $C_2$-$C_6$ alkynyl, or $C_1$-$C_6$ aralkyl;
Y is oxygen or sulfur; and
X is halide, or a pharmaceutically acceptable salt or prodrug thereof.

The pharmaceutical composition further includes a pharmaceutically effective carrier, and is preferably adapted for oral or parenteral administration to a mammalian patient, such as a human.

Additional embodiments include methods of treating a mammal, such as a human, by administering a pharmaceutical composition as described above.

DETAILED DESCRIPTION OF PREFERRED EMBODIMENTS

Compounds useful as the active ingredient in the inventive compositions have the general structural formula:

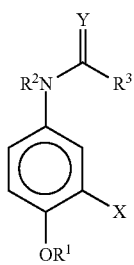

wherein
$R^1$ is hydrogen, $C_1$-$C_6$ alkyl, $C_2$-$C_6$ alkenyl, $C_2$-$C_6$ alkynyl, $C_2$-$C_7$ acyl, or $C_1$-$C_6$ aralkyl;
$R^2$ is hydrogen, $C_1$-$C_6$ alkyl, $C_2$-$C_6$ alkenyl, or $C_2$-$C_6$ alkynyl;
$R^3$ is $C_1$-$C_6$ alkyl, $C_2$-$C_6$ alkenyl, $C_2$-$C_6$ alkynyl, or $C_1$-$C_6$ aralkyl;
Y is oxygen or sulfur; and
X is a halide.

The term "alkyl" as used herein means a saturated monovalent hydrocarbon group (designated by the formula $C_nH_{2n+1}$) which is straight-chained, branched or cyclized ("cyclo alkyl") and which is unsubstituted or substituted, i.e., has had one or more of its hydrogens replaced by another atom or molecule. "Alkylene" means the divalent form of such a group.

"Alkenyl" means a linear, branched, or cyclized monovalent hydrocarbon containing at least one double bond, e.g., ethenyl, propenyl, and the like, and which is unsubstituted or substituted.

"Alkynyl" means a linear, branched, or cyclized monovalent hydrocarbon containing at least one triple bond, e.g., ethynyl, propynyl, and the like, and which is unsubstituted or substituted.

"Aryl" means a cyclized, monovalent, aromatic hydrocarbon having six (6) carbon atoms and which is unsubstituted or substituted, e.g. phenyl and the like, "Acyl" means a hydrogen, alkyl, alkenyl, alkynyl, or aryl, as defined above, connected, as substituents, via a carbonyl group. Examples include formyl, acetyl, propanoyl, benzoyl, and acryl. An acyl may be substituted or unsubstituted.

As used herein, "aralkyl" refer to an aryl group, as defined above, connected, as a substituent, via an alkylene group, as described above. The alkylene and aryl group of an aralkyl may be substituted or unsubstituted. Examples include but are not limited to benzyl and 2-phenylethyl.

"Halide" (or "halo") refers to a halogen atom, such as fluorine, chlorine, bromine, and iodine.

"Substituted" means that one or more hydrogen atoms on the designated atom is/are replaced with a selection from the indicated group, provided that the designated atom's normal valency is not exceeded, and that the substitution results in a stable compound.

"Unsubstituted" atoms bear all of the hydrogen atoms dictated by their valency, i.e., when a substituent is, for example, "keto" then two hydrogens on the carbon atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture and subsequent formulation into an efficacious therapeutic agent.

According to certain preferred embodiments, the halogen (X) in the formula above is preferably chlorine or bromine, and more preferably chlorine.

In some of these embodiments and in other preferred embodiments, $R_1$ is preferably hydrogen or methyl, more preferably hydrogen.

Similarly, in some of the aforementioned embodiments as well as in still other preferred embodiments, $R_2$ is preferably hydrogen or methyl, more preferably hydrogen.

Further, in some of the aforementioned embodiments as well as in still other preferred embodiments, $R_3$ is methyl or benzyl, more preferably methyl.

Preferably, Y is oxygen.

Most preferably, the active compound in the inventive compositions is 3-chloro-4-hydroxy-acetanilide.

The active compound in the inventive compositions may be used in the form of a pharmaceutically acceptable salt. As used herein, "pharmaceutically acceptable" refers to materials that are generally accepted as being suitable for administration to or contact with the human body or portions thereof.

Pharmaceutically acceptable salts are materials in which the parent compound is modified by making acid or base salts thereof. Examples of pharmaceutically-acceptable salts include, but are not limited to, mineral or organic acid salts of basic residues such as amines, or alkali or organic salts of acidic residues such as carboxylic acids.

Pharmaceutically acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Pharmaceutically acceptable salts are those forms of compounds, suitable for use in contact with the tissues of human beings and animals without causing excessive toxicity, irritation, allergic response, or other problems or complication, commensurate with a reasonable benefit/risk ratio.

Pharmaceutically acceptable salt forms of the active compounds provided herein are synthesized from the parent compound which contains a basic or acidic moiety by conventional chemical methods. Generally, such salts are prepared, for example, by reacting the free acid or base forms of these compounds with a stoichiometric amount of the appropriate base or acid in water or in an organic solvent, or in a mixture of the two. Generally, non aqueous media like ether, ethyl acetate, ethanol, isopropanol, or acetonitrile are preferred. Lists of suitable salts are found in *Remington's Pharmaceutical Sciences* (17th ed.), Mack Publishing Company, Easton, Pa., 1985, p. 1418, the disclosure of which is incorporated herein by this reference.

"Prodrugs" are any covalently bonded carriers which release the active parent drug in vivo when such prodrug is administered to a mammalian subject. Prodrugs of the compounds of the present invention are prepared by modifying functional groups present in the compounds in such a way that the modifications are cleaved, either in routine manipulation or in vivo, including by enzymatic conversion, to the parent compounds.

Prodrugs include compounds wherein hydroxyl or amine groups are bonded to any group that, when administered to a mammalian subject, cleaves to form a free hydroxyl or amino group, respectively. Examples or prodrugs include, but are not limited to, acetate, formate and benzoate derivatives of alcohol and amine functional groups in the active compounds of the present invention, and the like.

Compounds that function effectively as prodrugs of the compounds of the present invention may be identified using routine techniques known in the art. For examples of such prodrug derivatives, see, for example, (a) *Design of Prodrugs*, edited by H. Bundgaard, (Elsevier, 1985) and *Methods in Enzymology*, vol. 42, p. 309-396, edited by K. Widder et al. (Academic Press, 1985); (b) *A Textbook of Drug Design and Development*, edited by Krogsgaard-Larsen and H. Bundgaard, Chapter 5 "Design and Application of Prodrugs," by H. Bundgaard p. 113-191 (1991); (c) H. Bundgaard, *Advanced Drug Delivery Reviews*, 8, 1-38 (1992); (d) H. Bundgaard et al., *Journal of Pharmaceutical Sciences*, 77:285 (1988); and (e) N. Kakeya et al., *Chem. Pharm. Bull.*, 32: 692 (1984), each of which is specifically incorporated herein by reference.

In addition, the invention also includes solvates and metabolites of the active compound(s). The term "solvate" refers to an aggregate of a molecule with one or more solvent molecules. A "metabolite" is a pharmacologically active product produced through in vivo metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the invention includes metabolites of the active compounds, including compounds produced by a process comprising contacting a compound of this invention with a mammal for a period of time sufficient to yield a metabolic product thereof.

An "effective amount" of an active compound, when used in connection with the pharmaceutical compositions of the present invention, is an amount sufficient to produce a therapeutic result in a subject in need thereof. For example a therapeutic result can include, but is not limited to, treating or preventing pain in a subject or reducing fever in a subject.

In one aspect, the instant invention provides pharmaceutical compositions which contain a pharmaceutically effective amount of a compound together with a pharmaceutically acceptable carrier (e.g., a diluent, complexing agent, additive, excipient, adjuvant and the like). The active compound can be present, for example, in a salt form, a microcrystalline form, a nano-crystalline form, a co-crystalline form, a nanoparticulate form, a mirocparticulate form, and/or an amorphous form.

The carrier can be an organic or inorganic carrier that is suitable for enteral or parenteral applications. The active compound can be compounded, for example, with the usual non-toxic, pharmaceutically acceptable carriers for tablets, pellets, capsules, liposomes, solutions, emulsions, suspensions, and any other form suitable for such use, which are well known in the pharmaceutical formulation arts. Non-limiting examples of carriers that can be used include water, glucose, lactose, gum acacia, gelatin, mannitol, starch paste, magnesium trisilicate, talc, corn starch, keratin, colloidal silica, potato starch, microcrystalline cellulose, and other carriers suitable for use in manufacturing preparations, in solid, semisolid, or liquid form. In addition auxiliary, stabilizing, thickening and coloring agents and perfumes can be used. Particularly preferred compositions are adapted for oral or parenteral applications. In certain embodiments, the compositions can be adapted to give sustained release of the active compound.

In certain particularly preferred embodiments, the pharmaceutical compositions include, but are not limited to, those forms suitable for oral and parenteral (including intramuscular, intraperitoneal, subcutaneous, and intravenous) administration. The compositions can, where appropriate, be conveniently provided in discrete dosage units. The pharmaceutical compositions of the invention can be prepared by any of the methods well known in the pharmaceutical arts.

Pharmaceutical compositions suitable for oral administration include capsules, cachets, or tablets, each containing a predetermined amount of the active compound, generally as a powder or granules. In other embodiments, the oral composition is a solution, a suspension, or an emulsion. Alternatively, the compositions can be provided as a bolus, electuary, or paste.

Tablets and capsules for oral administration can contain conventional excipients such as binding agents, fillers, lubricants, disintegrating agents, colorants, flavoring agents, preservatives, or wetting agents. The tablets can be coated according to methods well known in the art, if desired. Oral liquid preparations include, for example, aqueous or oily suspensions, solutions, emulsions, syrups, or elixirs. Alternatively, the compositions can be provided as a dry product for constitution with water or another suitable vehicle before use. Such liquid preparations can contain conventional additives such as suspending agents, emulsifying agents, non-aqueous vehicles (which may include edible oils), preservatives, and the like.

The additives, excipients, and the like typically will be included in the compositions for oral administration within a range of concentrations suitable for their intended use or function in the composition, and which are well known in the pharmaceutical formulation art.

Pharmaceutical compositions for parenteral administration (e.g. by bolus injection or continuous infusion) can be provided in unit dose form in ampoules, pre-filled syringes, small volume infusion, or in multi-dose containers, and preferably include an added preservative. The compositions for parenteral administration can be suspensions, solutions, or emulsions, and can contain excipients such as suspending agents, stabilizing agents, and dispersing agents.

The additives, excipients, and the like typically will be included in the compositions for parenteral administration within a range of concentrations suitable for their intended use or function in the composition, and which are well known in the pharmaceutical formulation art.

In all embodiments of the inventive compositions, the active compounds are included in the compositions within a therapeutically useful and effective concentration range, as determined by routine methods that are well known in the medical and pharmaceutical arts.

Preferably, the active compound is present in an amount less than 500 mg, such as 50 mg or 100 mg. Most preferably, when the active compound is 3-chloro-4-hydroxy-acetanilide, 50 mg of the active compound is present in the pharmaceutical composition.

Pharmacokinetics

The pharmacokinetic behavior of the new drug exhibits increased bioavailability and will be independent of food uptake. The presence of food at the time of administration of the drug increases the Cmax by 77.25% $AUC_0$-Tmax by 23.5% and AUC0-∞ by 5.4%.

The novel drug will not make a substrate of CYP 1B2 and CYP 2C19 enzymes. The drug will also be an inhibitor of CYP 1B2, CYP 2B6, CYP 2C9, CYP 2D6, CYP 2E1 and CYP 3A. In addition, it is an inducer of CYP 1A2 and CYP 3A4.

It is pertinent to note that potassium $(K)_i$ plays a very important role in providing pain relief to the human body, but a number of promising drug candidates have failed to live up to expectations. For example, zoxazolamine was withdrawn in the year 1972 although it was approved by the USFDA in 1955 after being patented in 1953. Also, it is very important to note that it derived its activity from the primary amine that is $NH_2$ and eventually this primary amine was the cause of its hepatotoxicity.

One of the embodiments has a secondary amine, not a primary amine, as the most important pharmacological center.

Mode of Action

Next, the concept of the $I_k$ channel, which has a conductance of 2.280 PS, is expressed mainly in peripheral tissues, such as those of the hematopoietic system cells on the placenta, lung and pancreas. It is now well established that the sensation of pain is related to the increase in body temperature, and all the above four peripheral organs involving the peripheral tissues partake in the sense of a hyperactive $I_k$ channel. The Kca 3.1 channel in red blood cells was the first $Ca^{++}$ sensitive $K^+$ channel to be identified and it has been implicated in a wide range of cell functions, including vasodilation of the microvasculature, $K^+$ flux across endothelial cells of brain capillaries, and the phagocytic activity of neutrophils.

The reduction of pain is dependent on the value of Kca, which should not increase from 3.1, and the relationship between $K^+$ channels and cell proliferation is of ultimate importance.

It should be appreciated that the foregoing description of the embodiments has been provided for purposes of illustration. In other words, the subject disclosure it is not intended to be exhaustive or to limit the disclosure.

What is claimed is:

1. A pharmaceutical composition comprising a therapeutically effective amount of a compound of formula (I):

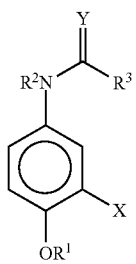

wherein
$R^1$ is hydrogen, $C_1$-$C_6$ alkyl, $C_2$-$C_6$ alkenyl, $C_2$-$C_6$ alkynyl, $C_2$-$C_7$ acyl, or $C_1$-$C_6$ aralkyl;
$R^2$ is hydrogen, $C_1$-$C_6$ alkyl, $C_2$-$C_6$ alkenyl, or $C_2$-$C_6$ alkynyl;
$R^3$ is $C_1$-$C_6$ alkyl, $C_2$-$C_6$ alkenyl, $C_2$-$C_6$ alkynyl, or $C_1$-$C_6$ aralkyl,
Y is oxygen or sulfur; and
X is halogen, or a pharmaceutically acceptable salt or prodrug thereof; a pharmaceutically effective carrier; and wherein said therapeutically effective amount is between non-zero and less than 500 mg.

2. The pharmaceutical composition according to claim 1, wherein the X is chlorine.

3. The pharmaceutical composition according to claim 1, wherein the $R^1$ is hydrogen.

4. The pharmaceutical composition according to claim 1, wherein the $R^2$ is hydrogen.

5. The pharmaceutical composition according to claim 1, wherein the $R^3$ is methyl.

6. The pharmaceutical composition according to claim 1, wherein the Y is oxygen.

7. The pharmaceutical composition according to claim 1, wherein the X is chlorine, $R_1$ is hydrogen, $R_2$ is hydrogen, $R_3$ is methyl, and Y is oxygen.

8. The pharmaceutical composition according to claim 1, wherein said compound is 3-chloro-4-hydroxy-acetanilide or a pharmaceutically acceptable salt thereof.

9. The pharmaceutical composition according to claim 1, wherein said therapeutically effective amount is about 50 mg.

10. The pharmaceutical composition according to claim 1, wherein said pharmaceutically composition is adapted for an oral administration.

11. The pharmaceutical composition according to claim 1, wherein said pharmaceutically composition is adapted for a parenteral administration.

12. A method of reducing a pain or increasing tolerance of a pain in a mammal, comprising: administering the therapeutically effective amount of the pharmaceutical composition according to claim 1 to the mammal.

13. A method of inhibiting production and/or release of one or more prostaglandins in a mammal, comprising: administering the therapeutically effective amount of the pharmaceutical composition according to claim 1 to the mammal.

14. A method of lowering a body temperature of a mammal, comprising: administering the therapeutically effective amount of the pharmaceutical composition according to claim 1 to the mammal.

15. A method of inhibiting at least one COX-dependent pathway in a mammal comprising administering the therapeutically effective amount of the pharmaceutical composition according to claim 1 to the mammal.

16. A method of inhibiting at least one NO pathway in a mammal, comprising: administering the therapeutically effective amount of the pharmaceutical composition according to claim 1 to the mammal.

17. The pharmaceutical composition according to claim 10, wherein said pharmaceutical composition is selected from a group consisting of a capsule, a cachet, a tablet, a solution, a suspension, an emulsion, a bolus, an electuary, and a paste.

18. The pharmaceutical composition according to claim 1, wherein the therapeutically effective amount of the pharmaceutical composition is configured to inhibit at least one NO pathway in a mammal.

19. The pharmaceutical composition according to claim 1, wherein the therapeutically effective amount of the pharmaceutical composition is configured to inhibit at least one COX-dependent pathway in a mammal.

20. The pharmaceutical composition according to claim 1, wherein the said therapeutically effective amount is about 50 mg.

* * * * *